United States Patent [19]

Krüger et al.

[11] Patent Number: 4,892,576
[45] Date of Patent: Jan. 9, 1990

[54] 6,7-DIHYDRO-PYRAZOLO (1,5-A)(1,3,5)TRIAZINE-2-SULPHONAMIDES, PROCESSES FOR THEIR PREPARATION AND THEIR USE AS HERBICIDES AND PLANT GROWTH REGULATORS

[75] Inventors: Martin Krüger; Jürgen Westermann; Friedrich Arndt; Richard Rees, all of Berlin, Fed. Rep. of Germany; Russel G. Hunt, Harston, England

[73] Assignee: Schering Aktiengesellschaft, Fed. Rep. of Germany

[21] Appl. No.: 213,905

[22] Filed: Jun. 30, 1988

[30] Foreign Application Priority Data

Jul. 1, 1987 [DE] Fed. Rep. of Germany ....... 3722072

[51] Int. Cl.$^4$ .................. A01N 43/14; A01N 43/66; A01N 43/68; C07D 251/00
[52] U.S. Cl. ........................................ 71/93; 544/113; 544/220
[58] Field of Search ............... 544/220, 113; 71/93

[56] References Cited

U.S. PATENT DOCUMENTS 4,734,414  3/1988  Kim ................................. 544/220

FOREIGN PATENT DOCUMENTS 0004171  9/1979  European Pat. Off. ............ 544/220
0142152  5/1985  European Pat. Off. ............ 544/220
0150974  8/1985  European Pat. Off. ............ 544/220
951652   3/1964  United Kingdom ............... 544/220

Primary Examiner—Mary C. Lee
Assistant Examiner—J. Richter
Attorney, Agent, or Firm—Ostrolenk, Faber, Gerb & Soffen

[57] ABSTRACT

The invention relates to new 6,7-dihydropyrazole-[1,5-a][1,3,5]triazine-2-sulphonamides of general formula I

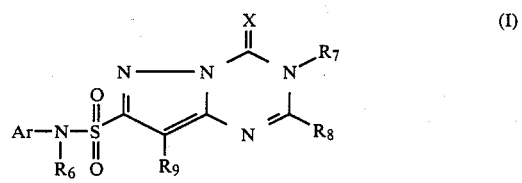

in which Ar, $R_6$, $R_7$, $R_8$, $R_9$ and X have the meanings given in the description, processes for their preparation and their use as herbicides and plant growth regulants.

16 Claims, No Drawings

6,7-DIHYDRO-PYRAZOLO (1,5-A)(1,3,5)TRIAZINE-2-SULPHONAMIDES, PROCESSES FOR THEIR PREPARATION AND THEIR USE AS HERBICIDES AND PLANT GROWTH REGULATORS

The invention relates to new 6,7-dihydropyrazolo-[1,5-a][1,3,5]triazine-2-sulphonamides, processes for their preparation and their use as herbicides and plant growth regulators.

It is known that triazolopyrimidinesulphonamides possess herbicidal activity (EP 142 152 and 150 974). However the herbicidal activity of the known compounds is not sufficient and/or selectivity problems can occur in important crops.

The object of the present invention is to make new compounds that do not show the disadvantages of the known compounds and have improved biological properties.

It has now been found that 6,7-dihydropyrazolo-[1,5-a][1,3,5]triazine-2-sulphonamides of general formula I

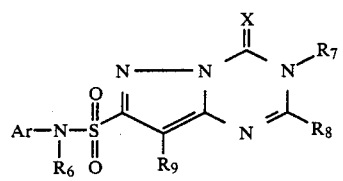

in which Ar is a phenyl, naphthyl, pyridyl or thienyl group of general formula

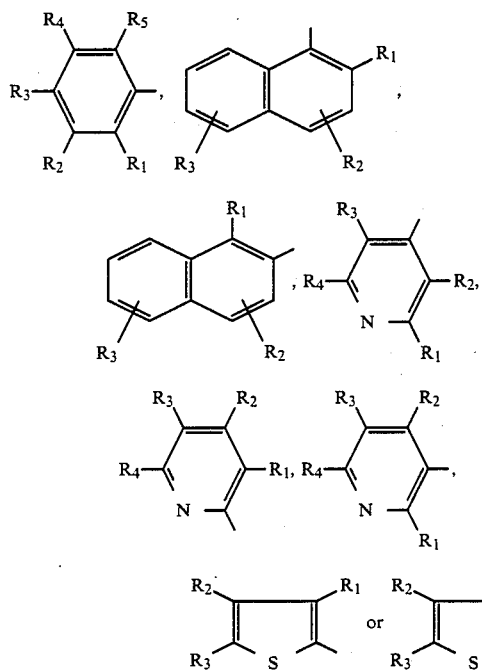

$R_1$, $R_2$, $R_3$, $R_4$ and $R_5$ are the same or different and are hydrogen, a $C_1$-$C_6$-alkyl, $C_2$-$C_6$-alkenyl or $C_2$-$C_6$-alkynyl group, each of which is optionally substituted by one or more of the same or different halo, hydroxy, halo-$C_1$-$C_4$-alkyl, $C_1$-$C_4$-alkoxy, halo-$C_1$-$C_4$-alkoxy, $C_1$-$C_4$-alkylthio, $C_1$-$C_4$-alkylsulphinyl or $C_1$-$C_4$-alkylsulphonyl, halogen, $C_1$-$C_4$-alkoxy, a group $R_{10}$—O—CO, sulphonyl, halogen, $C_1$-$C_4$-alkoxy, a group $R_{10}$—O—CO, a carbamoyl group $R_{11}R_{12}N$—CO—, an amino group $R_{10}$—S(O)$_n$—, an acyl group $R_{10}$—CO, a group $R_{10}$—O—CO—(CH$_2$)$_n$, or phenyl or phenoxy, both of which are optionally substituted by one or more of $C_1$-$C_4$-alkyl, halo or nitro, $R_6$ is hydrogen, an acyl group $R_{10}$—CO, a group $R_{10}$—O—CO—, $C_1$-$C_6$-alkyl, $C_2$-$C_6$-alkenyl, $C_2$-$C_6$-alkynyl, phenyl-$C_1$-$C_4$-alkyl, a carbamoyl group $R_{11}R_{12}N$—CO—, an alkali metal atom, a single metal equivalent of an alkaline earth or other metals or ammonium group, optionally substituted by $C_1$-$C_6$-alkyl, $R_7$ and $R_8$ are the same or different and are hydrogen, a $C_1$-$C_6$-alkyl, $C_2$-$C_6$-alkenyl or $C_2$-$C_6$-alkynyl group, each of which is optionally substituted by halo and/or $C_1$-$C_4$-alkoxy, a phenyl-$C_1$-$C_6$-alkyl, phenyl-$C_2$-$C_6$-alkenyl or phenyl-$C_2$-$C_6$-alkynyl group, each of which is optionally substituted by halo, $C_1$-$C_4$-alkyl, $C_1$-$C_4$-alkoxy, $C_1$-$C_4$-alkoxy-$C_1$-$C_4$-alkyl or halo-$C_1$-$C_4$-alkyl, phenyl, substituted by $R_1$, $R_2$, $R_3$, $R_4$ and $R_5$, an acyl group $R_{10}$—CO, a group $R_{10}$—O—CO, a group $R_{10}$—O—CO—(CH$_2$)$_n$, a carbamoyl group $R_{11}R_{12}N$—CO—, or a sulphonyl group $R_{10}$—SO$_2$, $R_9$ is hydrogen, a $C_1$-$C_6$-alkyl, $C_2$-$C_6$-alkenyl or $C_2$-$C_6$-alkynyl group, each of which is optionally substituted by halo and/or $C_1$-$C_4$-alkoxy, a phenyl-$C_1$-$C_6$-alkyl, phenyl-$C_2$-$C_6$-alkenyl or phenyl-$C_2$-$C_6$-alkynyl group, each of which is optionally substituted by halo, $C_1$-$C_4$-alkyl, $C_1$-$C_4$-alkoxy, $C_1$-$C_4$-alkoxy-$C_1$-$C_4$-alkyl or halo-$C_1$-$C_4$-alkyl, phenyl, substituted by $R_1$, $R_2$, $R_3$, $R_4$ and $R_5$, an acyl group $R_{10}$—CO, a group $R_{10}$—O—CO, a group $R_{10}$—O—CO—(CH$_2$)$_n$, a carbamoyl group $R_{11}R_{12}N$—CO—, a sulphonyl group $R_{10}$—SO$_2$ or $R_{10}$—O—SO$_2$, cyano or nitro $R_{10}$ is hydrogen, a $C_1$-$C_6$-alkyl, $C_2$-$C_6$-alkenyl, $C_2$-$C_6$-alkynyl or phenyl-$C_1$-$C_4$-alkyl group, each of which is optionally substituted by one or more of the same or different halo, hydroxy or $C_1$-$C_4$-alkoxy, or phenyl, optionally substituted by halo, nitro or $C_1$-$C_4$-alkyl, $R_{11}$ and $R_{12}$ are the same or different and are hydrogen, a $C_1$-$C_6$-alkyl, $C_2$-$C_6$-alkenyl or $C_2$-$C_6$-alkynyl group, each of which is optionally substituted by one or more of the same or different halo, hydroxy or $C_1$-$C_4$-alkoxy, or $R_{11}$ and $R_{12}$ together with the adjacent nitrogen form a pyrrolidinyl, piperidino or morpholino ring, X is oxygen or sulphur, and n is 0, 1 or 2, show an interesting herbicidal and plant growth regulant activity.

The term "halogen" in relationship with alkyl, alkenyl, alkynyl or phenyl means that one or more hydrogen atoms are replaced by one or more halogen atoms.

The term "halogen" means fluorine, chlorine, bromine and iodine.

6,7-Dihydropyrazolo[1,5-a][1,3,5]triazine-2-sulphonamides of general formula I which show particularly good activity are those in which Ar is a phenyl group of general formula

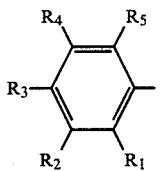

$R_1$ and $R_5$ are the same or different and are halogen, methyl, trifluoromethyl, nitro, methoxy or methoxycarbonyl, $R_2$, $R_3$ and $R_4$ are the same or different and are hydrogen, halogen, trifluoromethyl or a $C_1$–$C_4$-alkyl group, $R_6$ is hydrogen, a single equivalent of a metal or a $C_1$–$C_4$-acyl group, $R_7$ and $R_8$ are the same or different and are hydrogen, $C_1$–$C_4$-acyl, $C_1$–$C_6$-alkyl, $C_2$–$C_4$-alkenyl or phenyl, and $R_9$ is hydrogen, a $C_1$–$C_4$-acyl group, a group $R_{10}$—O—CO, a carbamoyl group $R_{11}R_{12}N$—CO—, a sulphonyl group $R_{10}$—$SO_2$, cyano or nitro.

The compounds of the invention of general formula I can be prepared for example by (A) reacting an amine of general formula II,

$$Ar-NH-R_6 \qquad (II)$$

in which Ar has the meaning given above and $R_6$ is hydrogen, $C_1$–$C_6$-alkyl, $C_2$–$C_6$-alkenyl or $C_2$–$C_6$-alkynyl, with a sulphonyl chloride of general formula III

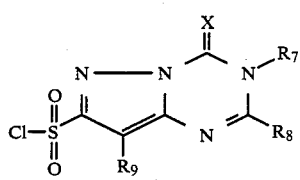

in which $R_7$, $R_8$, $R_9$ and X have the meanings given above in a suitable solvent and in the presence of an acid acceptor, or (B) reacting a compound of general formula IV

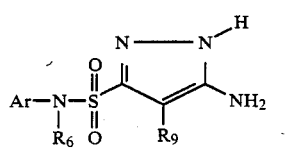

in which Ar and $R_9$ have the meaning given above and $R_6$ is hydrogen, $C_1$–$C_6$-acyl, $C_2$–$C_6$-alkenyl or $C_2$–$C_6$-alkynyl, with an isocyanate or isothiocyanate of formula V

$$R_7-NCX \qquad (V)$$

in which $R_7$ and X have the meanings given above in a suitable solvent, optionally in the presence of an acid acceptor and/or catalyst, and reacting the resulting compound of general formula VI

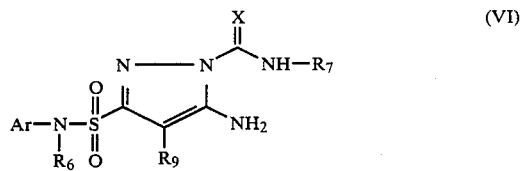

in which Ar, $R_7$, $R_9$ and X have the meanings given above and $R_6$ is hydrogen, $C_1$–$C_6$-alkyl, $C_2$–$C_6$-alkenyl or $C_2$–$C_6$-alkynyl, with an ortho ester of general formula VII

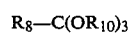
$$R_8-C(OR_{10})_3 \qquad (VII)$$

in which $R_{10}$ has the meaning given above, except hydrogen, and $R_8$ is hydrogen, a $C_1$–$C_6$-alkyl, $C_2$–$C_6$-alkenyl or $C_2$–$C_6$-alkynyl group, each of which is optionally substituted by halo and/or $C_1$–$C_4$-alkoxy, a phenyl-$C_1$–$C_6$-alkyl, phenyl-$C_2$–$C_6$-alkenyl or phenyl-$C_2$–$C_6$-alkynyl group, each of which is optionally substituted by halo, $C_1$–$C_4$-alkyl, $C_1$–$C_4$-alkoxy, $C_1$–$C_4$-alkoxy-$C_1$–$C_4$-alkyl or halo-$C_1$–$C_4$-alkyl, or phenyl, substituted by $R_1$, $R_2$, $R_3$, $R_4$ and $R_5$, in a suitable solvent, which can be the orthoester itself, or (C) reacting a compound of general formula IV

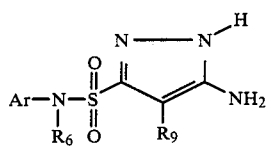

in which Ar and $R_9$ have the meaning given above and $R_6$ has the meaning given under (B), with an ortho ester of general formula VII

$$R_8-C(OR_{10})_3 \qquad (VII)$$

in which $R_8$ and $R_{10}$ have the meanings given under (B), in a suitable solvent, which can be the orthoester itself, to give a compound of formula VIII

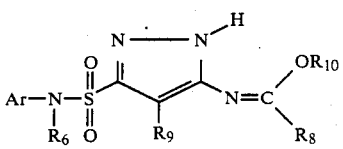

which is reacted with an isocyanate or isothiocyanate of formula V

$$R_7-NCX \qquad (V)$$

in which $R_7$ and X have the meanings given above in a suitable solvent, optionally in the presence of an acid acceptor and/or catalyst, or (D) reacting a compound of general formula IX

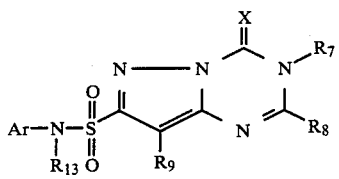

(IX)

in which Ar, $R_7$, $R_8$, $R_9$ and X have the meanings given above and $R_{13}$ is hydrogen or a single equivalent of a metal, with a compound of general formula X $$R_{10}-Hal \qquad (X)$$

or of general formula XI $$R_{10}-CO-Hal \qquad (XI)$$

in which $R_{10}$ has the meaning given above, except hydrogen and Hal is chlorine or bromine, or of general formula XII $$R_{10}-CO-O-COR_{10} \qquad (XII)$$

in which $R_{10}$ has the meaning given above, in a suitable solvent, or (E) reacting a compound of general formula XIII

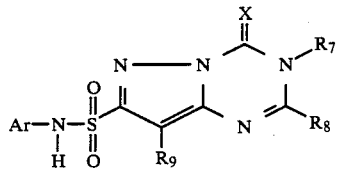

(XIII)

in which Ar, $R_7$, $R_8$, $R_9$ and X have the meanings given above, with a compound of general formula XIV $$M-Y \qquad (XIV)$$

in which M is a single equivalent of a metal, and Y is hydrogen, hydroxy, lower alkyl, lower alkoxy or an amino group, in a suitable solvent.

The particular reaction variants are preferably carried out in the presence of a diluent. For this purpose there are used solvents which are inert to the reactants.

Examples of such solvents or diluents are water, aliphatic, alicyclic and aromatic hydrocarbons, that can optionally be chlorinated, such as for example hexane, cyclohexane, petroleum ether, ligroin, benzene, toluene, methylene chloride, chloroform, carbon tetrachloride, ethylene dichloride and trichloroethane, ethers, such as for example diisopropyl ether, dibutyl ether, propylene oxide, dioxane and tetrahydrofuran, ketones such as for example acetone, methyl ethyl ketone, methyl isopropyl ketone and methyl isobutyl ketone, nitriles, such as for example acetonitrile and propionitrile, alcohols, such as for example methanol, ethanol, isopropanol, butanol and ethylene glycol, esters, such as for example ethyl acetate and amyl acetate, amides, such as for example dimethylformamide and dimethylacetamide, sulphones and sulphoxides, such as for example dimethyl sulphoxide and and sulpholane, and bases, such as for example pyridine.

The reaction is suitably carried out between room temperature and the boiling point of the particular reaction mixture. The reaction can be carried out under atmospheric pressure but if desired higher or lower pressures can be used.

Process variant A is preferably carried out in chlorinated hydrocarbons, such as dichloromethane or dichloroethane, in the presence of a catalyst and and/or acid acceptor. Examples of these are tertiary amines such as for example triethylamine, diisopropylethylamine, N-methylmorpholine, 4-dimethylaminopyridine and pyridine. Pyridine can be used both as catalyst and as a solvent.

Process variants B and C are preferably carried out in diluents such as, aliphatic, alicyclic and aromatic hydrocarbons, that can optionally be chlorinated, such as for example hexane, cyclohexane, petroleum ether, ligroin, benzene, toluene, methylene chloride, chloroform, carbon tetrachloride, ethylene dichloride and trichloroethane, ethers, such as for example diisopropyl ether, dibutyl ether, propylene oxide, dioxane and tetrahydrofuran, ketones such as for example acetone, methyl ethyl ketone, methyl isopropyl ketone and methyl isobutyl ketone, nitriles, such as for example acetonitrile and propionitrile, esters, such as for example ethyl acetate and amyl acetate, amide, such as for example dimethylformamide and dimethylacetamide, sulphones and sulphoxides, such as for example dimethyl sulphoxide and and sulpholane, and bases, such as for example pyridine, and optionally in the presence of a catalyst and and/or acid acceptor. Examples of these are tertiary amines such as for example triethylamine, diisopropylethylamine, N-methylmorpholine, 4-dimethylaminopyridine and pyridine.

Process variant D is preferably carried out by reacting a compound of general formula IX in a suitable solvent with a compound of general formula X, XI or XII, filtering off the salts which as general rule are highly insoluble and recovering the desired compounds after evaporation of the solvent.

Process variant E is preferably carried out by reacting a compound of general formula XIII in a suitable solvent with a metal base, such as a metal hydroxide, metal hydride, metal alkyl or metal amide, and the salts which as a general rule are highly insoluble can be recovered by filtration or by evaporation of the solvent.

The compounds of the invention prepared by these processes can be isolated from the reaction mixtures in conventional manner, for example by distillation of the solvent at normal or reduced poressure, by precipitation with water or by extraction.

A higher level of purity can be achieved as a rule by column chromatography as well as by fractional distillation or crystallisation.

The compounds of the invention are, as a rule, colorless or odourless crystals that are slightly soluble in water and in aliphatic hydrocarbons such as petroleum ether, hexane, pentane and cyclohexane and highly soluble in halogenated hydrocarbons, such as chloroform, methylene chloride and carbon tetrachloride, aromatic hydrocarbons such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The sulphonyl chlorides of general formula III are new and can be prepared as described in the literature or by known methods by reacting a 2-benzylthio-6,7-dihydropyrazolo[1,5-a][1,3,5]triazin-7-one of general formula XV

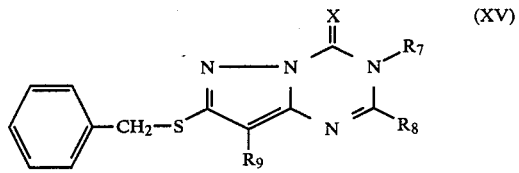

(XV)

in which $R_7$, $R_8$, $R_9$ and X have the meanings given above, with chlorine in water or a water/acetic acid mixture.

Amines of general formula II, isocyanates and isothiocyanates of general formula V and orthoesters of general formula VII are in the main commercially available or can be prepared by known processes or as described in the literature.

The compounds of the invention influence plant growth and can therefore be used as plant growth regulators and especially as herbicides. Surprisingly, the compounds of the invention show a wide activity against monocotyledonous and dicotyledonous weeds with good selectivity in crops. Whether the compounds of the invention act as total or selective herbicides depends mainly on the rates of use but also on the species and the time of use.

The compounds can be used in seed treatments, and in pre or post emergent use.

The compounds of the invention can used for example against the following plant species:

Dicotyledonous weeds of the species *Polygonum, Sinapis, Atriplex, Spergula, Stellaria, Galium, Viola, Cirsium, Amaranthus, Ipomoea, Xanthium, Abutilon, Chenopodium, Cassia, convolvulus, Mentha, Veronica, Matricaria, Solanum, Lamium, Thlapsi, Capsella, Datura, Galinsoga, Mercurialis, Rhaphanus, Vicia, Portulaca, Physalis, Sida, Anoda, Euphorbia, Myosotis, Centaurea, Brassica, Chrysanthemum* and *Helianthus;*

Monocotyledonous weeds of the species *Echinochloa, Setaria, Panicum, Digitaria, Phleum, Poa, Festuca, Eleusine Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Agrostis, Alopecurus, Apera, Rottoboellia, Triticum* and *Hordeum.*

The compounds can be used in important agricultural crops, such as wheat, barley, rice and cotton.

The use of the compounds of the invention is not limited to the weeds and crops mentioned above but can also be applied in a similar way to other plants.

The compounds are also suitable for weed control in industrial and railway installations and also roads and verges, with or without vegetation, in forests, woodlands, berry fruit and hop installations, as well as plantations.

The rates of use can vary over a wide range. They depend generally on the nature of the desired effects. In general the rates of use lie between 0.01 and 5 kg of active ingredient per hectare and preferably for example in weed control between 0.1 and 0.5 kg of active ingredient per hectare.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added. Herbicidally active mixing partners suitable in this connection include for example, the active agents listed in Weed Abstracts, vol. 34, No. 5 (1986) under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

Suitable mixture partners may include phospholipids, e.g. phosphatidylcholine, hydrated phosphatidylcholines phosphatidylethanolamine, N-acyl-phosphatidylethanolamines, phosphatidylinositol, phosphatidylserine, lysolecithin or phosphatidylglycerol.

The designated active ingredients or their mixtures can suitable be used, for example, as powders, dusts, granules, solutions, emulsions or suspensions, with the addition of liquid and/or solid carriers and/or diluents and, optionally, binding, wetting emulsifying and/or dispersing adjuvants.

Suitable liquid carriers are, for example aliphatic and aromatic hydrocarbons, such as benzene, toluene, xylene, cyclohexanone, isophorone, dimethyl sulphoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

(A) Wettable Powder (1) 25 percent by weight active ingredient
60 percent by weight kaolin
10 percent by weight silicic acid
5 percent by weight of a mixture of calcium lignosulphonate and the sodium salt of N-methyl-N-oleyltaurine (2) 40 percent by weight active ingredient
25 percent by weight bentonite
25 percent by weight colloidal silicic acid
10 percent by weight of a mixture of calcium lignosulphonate and alkylphenyl polyglycol ether (B) Paste 45 percent by weight active ingredient
5 percent by weight sodium aluminium silicate 15 percent by weight cetyl polyglycol ether with 8 mol of ethylene oxide
2 percent by weight spindle oil
10 percent by weight polyethylene glycol
23 percent by weight water (C) Emulsifiable Concentrate 25 percent by weight active ingredient
15 percent by weight cyclohexanone
55 percent by weight xylene
5 percent by weight of a mixture of calcium dodecylbenzenesulphonate and nonylphenolpolyoxyethylene.

The following examples illustrate the preparation of compound according to the invention.

EXAMPLE 1

N-(2,6-Dichlorophenyl)-6,7-dihydro-5,6-dimethyl-3-methoxycarbonyl-7-oxopyrazolo[1,5-a][1,3,5]triazine-2-sulphonamide (process A)

2.84 g (17.5 mmol) 2,6-Dichloroaniline was stirred in 15 ml pyridine with 5.00 g (15.6 mmol) 6,7-dihydro-5,6-dimethyl-3-methoxycarbonyl-7-oxopyrazolo[1,5-a][1,3,5]-triazine-2-sulphonyl chloride for 15 hours at 50° C. and the undissolved residue filtered. The filtrate was concentrated, the residue treated with 2N sulphuric acid, the product suction filtered, chromatographed with hexane/ethyl acetate over silica gel and recrystallised from ethyl acetate.

Yield: 1.97 g=28% of theory.
M.p.: 265°–267° C.
Elementary analysis
Calc. (%): C 40.37 H 2.94 N 15.69 S 7.19 Cl 15.89.
Found (%): C 40.45 H 3.34 N 14.94 S 7.21 Cl 15.70.

Preparation of the starting material for Example 1

(a)

6,7-Dihydro-5,6-dimethyl-3-methoxycarbonyl-7-oxopyrazolo[1,5-a][1,3,5]triazine-2-sulphonyl chloride 15.50 g (43 mmol) 2-Benzylthio-6,7-dihydro-3-methoxycarbonyl-5,6-dimethyl-7-oxopyrazolo[1,5-a][1,3,5]triazine-7-thione was suspended in 200 ml water/acetic acid (1:1 mixture). At 10° C., chlorine was introduced over 3 hours. The product was extracted with methylene chloride and dried over magnesium sulphate. After concentrating, the residue was treated with ether and the product suction filtered.

Yield: 9.70 g=70% of theory.
M.p.: 188°–190° C.

(b)

2-Benzylthio-6,7-dihydro-3-methoxycarbonyl-5,6-dimethyl-7-oxopyrazolo[1,5-a][1,3,5]triazine-7-thione 6.77 g (20.1 mmol) 5-Amino-B 3-benzylthio-4-methoxycarbonyl-N-methylpyrazole-1-carbothioamide was stirred in 35 ml triethyl orthoacetate allowing the ethanol which formed to distil off. After cooling, the product was suction filtered, washed with ether and dried.

Yield: 5.35 g=74% of theory.
M.p.: 212°–213° C.
Elementary analysis Calc. (%): C 53.51 H 4.47 N 15.54 S 17.79. Found (%): C 53.37 H 4.27 N 15.56 S 18.11.

(c)

5-Amino-3-benzylthio-4-methoxycarbonyl-N-methylpyrazole-1-carbothioamide 45.11 g (0.127 mol) Methyl 3,3-dibenzylthio-2-cyanoacrylate and 13.35 g (0.127 mol) 4-methylthiosemicarbazide in 225 ml ethanol were heated under reflux for 10 hours. After cooling, the product was suction filtered, washed with ether and dried.

Yield: 33.61 g=79% of theory.
M.p.: 162°–163° C.
Elementary analysis Calc. (%): C 49.98 H 4.79 N 16.65 S 19.06. Found (%): C 50.00 H 5.12 N 16.78 S 19.48.

(d) Methyl 3,3-dibenzylthio-2-cyanoacrylate

A solution of sodium methanolate was prepared from from 80.49 g (3.5 mol) sodium and 1050 ml methanol. 200.2 g (2.0 mol) of 99% methyl 2-cyanoacrylate was dissoved on 600 ml of this solution, the mixture cooled to 5° C. and 60 ml (1.0 mol) carbon disulphide added, dropwise, under cooling. A further 300 ml of the methanolate solution was added and the mixture cooled to 10° C. 30 ml (0.5 mol) Carbon disulphide was added dropwise, after which the remaining methanolate solution was added, and finally a further 15.75 ml (0.25 mol) carbon disulphide was added, dropwise. The mixture was stirred for 30 minutes at 15° C. 598.68 g (3.5 mol) Benzyl bromide was added dropwise, with cooling. The mixture was stirred for 2 hours at 20° C., the solvent distilled and the residue treated with ice-water. The product was suction filtered, washed with water and ether and dried.

Yield: 521.2 g=84% of theory.
M.p.: 100°–101° C.
Elementary analysis Calc. (%): C 64.19 H 4.82 N 3.94 S 18.04. Found (%): C 64.14 H 4.82 N 4.18 S 17.82.

EXAMPLE 2

N-(2,6-Difluorophenyl)-6,7-dihydro-5,6-dimethyl-3-methoxycarbonyl-7-thioxopyrazolo[1,5-a][1,3,5]triazine-2-sulphonamide (process C)

2.6 g (6.7 mmol) N-(2,6-difluorophenyl)-4-methoxycarbonyl-5-(1-methoxyethylidenamino)pyrazole-3-sulphonamide was stirred with 20 ml tetrahydrofuran, 0.88 ml (12 mmol) methyl isothiocyanate and 0.71 ml (7 mmol) triethylamine for 8 hours at 50° C. The mixture was cooled to 5° C., the crystals suction filtered and washed with tetrahydrofuran and ether.

Yield: 1.5 g=52% of theory.
M.p.: 284°–286° C.
Elementary analysis Calc. (%): C 41.95 H 3.05 N 16.31 S 14.93 F 8.85. Found (%): C 41.89 H 3.49 N 16.23 S 15.09 F 8.91.

Preparation of the starting material for Example 2

(a)

N-(2,6-Difluorophenyl)-4-methoxycarbonyl-5-(1-methoxyethylidenamino)pyrazole-3-sulphonamide 5.0 g (15mmol) 5-amino-N-(2,6-difluorophenyl)-4-methoxycarbonylpyrazole-3-sulphonamide was heated under reflux with 50 ml acetonitrile, 2.1 ml (17.5 mmol) triethyl orthoacetate and 3 drops acetic acid for 8 hours. The undissolved residue was filtered and the filtrate concentrated. The residue was chromatographed with hexane/ethyl acetate over silica gel and recrystallised from ether.

Yield: 4.8 g=82% of theory.
M.p.: 194°–196° C.
Elementary analysis Calc. (%): C 43.30 H 3.63 N 14.43 S 8.26 F 9.78. Found (%): C 43.27 H 3.98 N 14.13 S 8.09 F 9.69.

(b)
5-Amino-N-(2,6-difluorophenyl)-4-methoxycarbonyl-pyrazole-3-sulphonamide 7.50 g (20 mmol) 5-acetamido-N-(2,6-difluorophenyl)-4-methoxycarbonylpyrazole-3-sulphonamide was suspended in 80 ml 4.4N methanolic hydrochloric acid and heated under reflux for 5 hours. The solvent was distilled and the residue treated with water. The product was suction filtered, washed with water and dried.
Yield: 6.2 g=93% of theory.
M.p.: 265°–266° C.
Elementary analysis Calc. (%): C 39.76 H 3.03 N 16.86 S 9.65 F 11.44. Found (%): C 40.23 H 3.25 N 17.12 S 9.80 F 11.46.

(c)
5-Acetamido-N-(2,6-difluorophenyl)-4-methoxycarbonylpyrazole-3-sulphonamide 23.63 g (177.5 mmol) of 97% 2,6-difluoroaniline and 1.48 g N,N-dimethyl-4-aminopyridine was dissolved in 225 ml pyridine and 25.0 g (88.75 mmol) 5-acetamido-4-methoxycarbonylpyrazole-3-sulphonyl chloride added portionwise. The mixture was stirred for 48 hours at 25° C. The pyridine was distilled and the residue dissolved in 510 ml methylene chloride washed twice with 370 ml 5N hydrochloric acid and twice with 370 ml water, dried over magnesium sulphate and concentrated. The residue was triturated with ether, the product suction filtered, washed with ether and dried.
Yield: 17.53 g=53% of theory.
M.p.: 221°–222° C.
Elementary analysis Calc. (%): C 41.71 H 3.23 N 14.97 S 8.57 F 10.15. Found (%): C 41.66 H 3.30 N 14.83 S 8.54 F 10.23.

(d)
5-Acetamido-4-methoxycarbonylpyrazole-3-sulphonyl chloride 73.0 g (239 mmol) Methyl 5-acetamido-3-benzylthiopyrazole-4-carboxylate was dissolved in 470 ml methylene chloride and treated with 124.15 g silica gel and 25.6 g water and cooled to 0° C. 160.6 g (1.19 mol) Sulphuryl chloride in 730 ml methylene chloride was added dropwise. The mixture was stirred for 3 hours at 0° C., filtered, washed several times with methylene chloride, dried over magnesium sulphate and concentrated. The residue was triturated with ether/hexane, the crystals suction filtered, washed with hexane and dried.
Yield: 51.9 g=77% of theory.
M.p.: 143°–144° C.
Elementary analysis Calc. (%): C 29.85 H 2.86 N 14.92 S 11.38 F 12.59. Found (%): C 29.92 H 2.76 N 14.87 S 11.40 F 12.51.

(e) Methyl 5-acetamido-3-benzylthiopyrazole-4-carboxylate 70.5 g (0.27 mol) Methyl 5-amino-3-benzylthiopyrazole-4-carboxylate was dissolved at 80° C. in 135 ml glacial acetic acid and treated with 27.75 g (0.27 mol) acetic anhydride. The solution was heated under reflux for 7 hours and concentrated. The residue was recrystallised from ether, the crystals suction filtered, washed with ether and dried.
Yield: 73.2 g=89% theory.
M.p.: 136°–137° C.
Elementary analysis Calc. (%): C 55.07 H 4.95 N 13.76 S 10.50. Found (%): C 55.17 H 4.77 N 13.80 S 10.79.

(f) Methyl 5-amino-3-benzylthiopyrazole-4-carboxylate 124.34 g (0.35 mol) Methyl 3,3-dibenzylthio-2-cyanoacrylate and 46.70 g (0.35 mol) t-butyl hydrazinoformate was heated under reflux for 3.5 hours in 700 ml ethanol and concentrated. The residue was treated with 700 ml glacial acetic acid and stirred for 3 hours at 110° C. and for 1 hour at 5° C. The product was suction filtered, washed with glacial acetic acid and hexane and dried.
Yield: 70.9 g=77% of theory.
M.p.: 111°–112° C.
Elementary analysis Calc. (%): C 54.73 H 4.97 N 15.96. Found (%): C 54.02 H 4.68 N 15.93.

EXAMPLE 3

N-(2,6-Difluorophenyl)-6,7-dihydro-5,6-dimethyl-3-methoxycarbonyl-7-oxopyrazolo[1,5-a][1,3,5]triazine-2-sulphonamide (process C)

1.5 g (3.9 mmol) N-(2,6-difluorophenyl)-4-methoxycarbonyl-5-(1-methoxyethylidenamino)pyrazole-3-sulphonamide was stirred with 20 ml tetrahydrofuran, 0.29 g (5.0 mmol) methyl isocyanate and 0.39 ml (3.9 mmol) triethylamine for 48 hours at 25° C. The crystals were suction filtered and washed with tetrahydrofuran and ether.
Yield: 1.3 g=81% of theory.
M.p.: 257°–259° C.
Elementary analysis Calc. (%): C 43.58 H 3.17 N 16.94 S 7.76 F 9.19. Found (%): C 43.34 H 3.23 N 16.80 S 7.53 F 9.03.

In a similar manner to Examples 1 to 3 the following compounds of the invention were prepared were prepared.

| Example No | Name of Compound | Physical Constant |
|---|---|---|
| 4 | N—(2,6-Dichlorophenyl)-6,7-dihydro-5,6-dimethyl-3-methoxycarbonyl-7-thioxo-pyrazolo[1,5-a][1,3,5]triazine-2-sulphonamide | mp:304–305° C. |
| 5 | N—(2,6-Dichloro-3-methylphenyl)-6,7-dihydro-5,6-dimethyl-3-methoxycarbonyl-7-oxo-pyrazolo[1,5-a][1,3,5]triazine-2-sulphonamide | mp:262–264° C. |
| 6 | N—(2,6-Dichloro-3-methylphenyl)-6,7-dihydro-5,6-dimethyl-3-methoxycarbonyl-7-thioxo-pyrazolo[1,5-a][1,3,5]triazine-2-sulphonamide | mp:312–314° C. |
| 7 | N—(2-Chloro-6-fluorophenyl)-6,7-dihydro-5,6-dimethyl-3-methoxycarbonyl-7-oxo-pyrazolo[1,5-a][1,3,5]triazine-2-sulphonamide | mp:240–242° C. |
| 8 | N—(2-Chloro-6-fluorophenyl)-6,7-dihydro-5,6-dimethyl-3-methoxycarbonyl-7-thioxo-pyrazolo[1,5-a][1,3,5]triazine-2-sulphonamide | mp:285–286° C. |
| 9 | N—(2-Chloro-6-methylphenyl)-6,7-dihydro-5,6-dimethyl-3-methoxycarbonyl-7-oxo-pyrazolo[1,5-a][1,3,5]triazine-2-sulphonamide | mp:259–261° C. |
| 10 | N—(2-Chloro-6-methylphenyl)-6,7-dihydro-5,6-dimethyl-3-methoxycarbonyl-7-thioxo-pyrazolo[1,5-a][1,3,5]triazine-2-sulphonamide | mp:295–297° C. |
| 11 | N—(2,6-Dibromophenyl)-6,7-dihydro-5,6-dimethyl-3-methoxycarbonyl-7-oxo-pyrazolo[1,5-a][1,3,5]triazine-2-sulphonamide | mp:293–295° C. |
| 12 | N—(2,6-Dibromophenyl)-6,7-dihydro- | mp:327– |

-continued

| Example No | Name of Compound | Physical Constant |
|---|---|---|
| | 5,6-dimethyl-3-methoxycarbonyl-7-thioxo-pyrazolo[1,5-a][1,3,5]triazine-2-sulphonamide | 330° C. |
| 13 | N—(2-Methyl-6-nitrophenyl)-6,7-dihydro-5,6-dimethyl-3-methoxycarbonyl-7-oxo-pyrazolo[1,5-a][1,3,5]triazine-2-sulphonamide. hydrate | mp:230–232° C. |
| 14 | N—(2-Methyl-6-nitrophenyl)-6,7-dihydro-5,6-dimethyl-3-methoxycarbonyl-7-thioxo-pyrazolo[1,5-a][1,3,5]triazine-2-sulphonamide | mp:271–274° C. |
| 15 | 6,7-Dihydro-5,6-dimethyl-3-methoxycarbonyl-N—(2-methoxycarbonyl-6-methylphenyl)-7-thioxo-pyrazol[1,5-a][1,3,5]triazine-2-sulphonamide | mp:210–212° C. |
| 16 | N—(2-Bromo-6-methoxyphenyl)-6,7-dihydro-5,6-dimethyl-3-methoxycarbonyl-7-thioxo-pyrazolo[1,5-a][1,3,5]triazine-2-sulphonamide, x hydrate | mp:276–278° C. |
| 17 | N—(2,6-Dichlorophenyl)-6,7-dihydro-5,6-dimethyl-3-ethoxycarbonyl-7-oxo-pyrazolo[1,5-a][1,3,5]triazine-2-sulphonamide | mp:283–284° C. |
| 18 | N—(2,6-Difluorophenyl)-6,7-dihydro-5,6-dimethyl-3-ethoxycarbonyl-7-oxo-pyrazolo[1,5-a][1,3,5]triazine-2-sulphonamide | mp:221–223° C. |
| 19 | N—(2-Chloro-6-fluorophenyl)-6,7-dihydro-5,6-dimethyl-3 ethoxycarbonyl-7-oxo-pyrazolo[1,5-a][1,3,5]triazine-2-sulphonamide | mp:214–217° C. |
| 20 | N—(2,6-Dichloro-3-methylphenyl)-6,7-dihydro-5,6-dimethyl-3-ethoxycarbonyl-7-oxo-pyrazolo[1,5-a][1,3,5]triazine-2-sulphonamide | mp:228–230° C. |
| 21 | N—(2,6-Dibromophenyl)-6,7-dihydro-5,6-dimethyl-3-ethoxycarbonyl-7-oxo-pyrazolo[1,5-a][1,3,5]triazine-2-sulphonamide | mp:295–297° C. |
| 22 | N—(2-Bromo-6-chlorophenyl)-6,7-dihydro-5,6-dimethyl-3-ethoxycarbonyl-7-oxo-pyrazolo[1,5-a][1,3,5]triazine-2-sulphonamide | mp:285–286° C. |
| 23 | N—(2,6-Dichlorophenyl)-6,7-dihydro-5,6-dimethyl-3-ethoxycarbonyl-7-thioxo-pyrazolo[1,5-a][1,3,5]triazine-2-sulphonamide | mp:272–274° C. |
| 24 | 6,7-Dihydro-5,6-dimethyl-3-ethoxycarbonyl-N—(2-methoxycarbonyl-6-methyphenyl)-7-thioxo-pyrazolo[1,5-a][1,3,5]triazine-2-sulphonamide | mp:182–186° C. |
| 25 | N—(2,6-Dichloro-3-methylphenyl)-6,7-dihydro-5,6-dimethyl-3-ethoxycarbonyl-7-thioxo-pyrazolo[1,5-a][1,3,5]triazine-2-sulphonamide | mp:257–259° C. |
| 26 | N—(2-Chloro-6-fluorophenyl)-6,7-dihydro-5,6-dimethyl-3-ethoxycarbonyl-7-thioxo-pyrazolo[1,5-a][1,3,5]triazine-2-sulphonamide | mp:232–235° C. |
| 27 | N—(2,6-Difluorophenyl)-6,7-dihydro-5,6-dimethyl-3-ethoxycarbonyl-7-thioxo-pyrazolo[1,5-a][1,3,5]triazine-2-sulphonamide | mp:214–216° C. |
| 28 | N—(2-Chloro-6-methylphenyl)-6,7-dihydro-5,6-dimethyl-3-ethoxycarbonyl-7-thioxo-pyrazolo[1,5-a][1,3,5]triazine-2-sulphonamide | mp:225–226° C. |
| 29 | N—(2,6-Dibromophenyl)-6,7-dihydro-5,6-dimethyl-3-ethoxycarbonyl-7-thioxo-pyrazolo[1,5-a][1,3,5]triazine-2-sulphonamide | mp:285–287° C. |
| 30 | N—(2-Bromo-6-chlorophenyl)-6,7-dihydro-5,6-dimethyl-3-ethoxycarbonyl-7-thioxo-pyrazolo[1,5-a][1,3,5]triazine-2-sulphonamide | mp:291–293° C. |
| 31 | 3-Cyano-N—(2,6-dichlorophenyl)-6,7-dihydro-5,6-dimethyl-7-oxopyrazolo-[1,5-a][1,3,5]triazine-2-sulphonamide | mp:338–341° C. |
| 32 | 3-Cyano-N—(2,6-dibromophenyl)-6,7-dihydro-5,6-dimethyl-7-oxopyrazolo-[1,5-a][1,3,5]triazine-2-sulphonamide | mp: 303 (dec) |
| 33 | 3-Cyano-N—(2,6-dichloro-3-methylphenyl)-6,7-dihydro-5,6-dimethyl-7-oxopyrazolo[1,5-a][1,3,5]triazine-2-sulphonamide | mp:298–303° C. |
| 34 | 3-Cyano-6,7-dihydro-5,6-dimethyl-N—(2-methoxycarbonyl-6-methylphenyl)-7-oxo-pyrazolo[1,5-a][1,3,5]triazine-2-sulphonamide | mp:258–262° C. |
| 35 | 3-Cyano-N—(2,6-dichlorophenyl)-6,7-dihydro-5,6-dimethyl-7-thioxopyrazolo-[1,5-a][1,3,5]triazine-2-sulphonamide | mp:279–282° C. |
| 36 | 3-Cyano-N—(2,6-dichloro-3-methylphenyl)-6,7-dihydro-5,6-dimethyl-7-thioxopyrazolo-[1,5-a][1,3,5]triazine-2-sulphonamide | mp:272–273° C. |
| 37 | 3-Cyano-N—(2,6-dibromophenyl)-6,7-dihydro-5,6-dimethyl-7-thioxopyrazolo-[1,5-a][1,3,5]triazine-2-sulphonamide | mp:300° C. (dec) |
| 38 | 3-Cyano-6,7-dihydro-5,6-dimethyl-N—(2-methoxycarbonyl-6-methylphenyl)-7-thioxo-pyrazolo[1,5-a][1,3,5]triazine-2-sulphonamide | mp:248–249° C. |
| 39 | 3-Carbamoyl-N—(2,6-dichlorophenyl)-6,7-dihydro-5,6-dimethyl-7-oxopyrazolo-[1,5-a][1,3,5]triazine-2-sulphonamide | mp:303–305° C. |
| 40 | 3-Carbamoyl-N—(2,6-dichloro-3-methylphenyl)-6,7-dihydro-5,6-dimethyl-7-oxopyrazolo-[1,5-a][1,3,5]triazine-2-sulphonamide | mp:307° C. (dec) |
| 41 | 3-Carbamoyl-N—(2,6-dibromophenyl)-6,7-dihydro-5,6-dimethyl-7-oxopyrazolo-[1,5-a][1,3,5]triazine-2-sulphonamide | mp:274–275° C. |
| 42 | 3-Carbamoyl-N—(2,6-dichlorophenyl)-6,7-dihydro-5,6-dimethyl-7-thioxopyrazolo-[1,5-a][1,3,5]triazine-2-sulphonamide | mp:295–296° C. |
| 43 | 3-Carbamoyl-N—(2,6-dichloro-3-methylphenyl)-6,7-dihydro-5,6-dimethyl-7-thioxopyrazolo-[1,5-a][1,3,5]triazine-2-sulphonamide | mp:269° C. (dec) |
| 44 | 3-Carbamoyl-N—(2,6-dibromophenyl)-6,7-dihydro-5,6-dimethyl-7-thioxopyrazolo-[1,5-a][1,3,5]triazine-2-sulphonamide | mp:279–280° C. |
| 45 | N—(2,6-Dichlorophenyl)-6,7-dihydro-5,6-dimethyl-3-methylsulphonyl-7-oxopyrazolo-[1,5-a][1,3,5]triazine-2-sulphonamide | mp:289–292° C. |
| 46 | N—(2,6-Dichloro-3-methylphenyl)-6,7-dihydro-5,6-dimethyl-3-methylsulphonyl-7-oxopyrazolo-[1,5-a][1,3,5]triazine-2-sulphonamide | mp:273–275° C. |
| 47 | N—(2,6-Dichlorophenyl)-6,7-dihydro-5,6-dimethyl-3-methylsulphonyl-7-thioxo-pyrazolo[1,5-a][1,3,5]triazine-2-sulphonamide | mp:318–320° C. |
| 48 | N—(2,6-Dichloro-3-methylphenyl)-6,7-dihydro-5,6-dimethyl-3-methylsulphonyl-7-thioxo-pyrazolo[1,5-a][1,3,5]triazine-2-sulphonamide | mp:290–293° C. |
| 49 | 6,7-Dihydro-5,6-dimethyl-3-methoxycarbonyl-N—(2-methoxycarbonyl-6-methylphenyl)-7-oxo-pyrazolo[1,5-a][1,3,5]triazine-2-sulphonamide | |
| 50 | N—(2-Bromo-6-methoxyphenyl)-6,7-dihydro-5,6-dimethyl-3-methoxycarbonyl-7-oxo-pyrazolo[1,5-a][1,3,5]triazine-2-sulphonamide | |
| 51 | 6,7-Dihydro-5,6-dimethyl-3-methoxycarbonyl-7-oxo-N—(2-trifluoromethylphenyl)-pyrazolo[1,5-a][1,3,5]triazine-2-sulphonamide | |
| 52 | 6,7-Dihydro-5,6-dimethyl-N—(5,6-dimethyl-2-nitrophenyl)-3-methoxycarbonyl-7-oxo pyrazolo[1,5-a][1,3,5]triazine-2-sulphonamide | |
| 53 | N—(2-Bromo-6-chlorophenyl)-6,7-dihydro-5,6-dimethyl-3-methoxycarbonyl-7-oxo-pyrazolo[1,5-a][1,3,5]triazine-2-sulphonamide | |
| 54 | N—(2-Bromo-6-chloro-3-methylphenyl)-6,7-dihydro-5,6-dimethyl-3-methoxycarbonyl-7-oxopyrazolo[1,5-a][1,3,5]triazine-2-sulphonamide | |
| 55 | N—(2-Bromo-6-chloro-5-methylphenyl)-6,7-dihydro-5,6-dimethyl-3-methoxycarbonyl-7-oxopyrazolo[1,5-a][1,3,5]triazine-2-sulphonamide | |
| 56 | N—(2,6-Dibromo-3-methylphenyl)-6,7-dihydro-5,6-dimethyl-3-methoxycarbonyl-7-oxo-pyrazolo[1,5-a][1,3,5]triazine-2-sulphonamide | |
| 57 | 6,7-Dihydro-5,6-dimethyl-3-methoxycarbonyl N—(6-methyl-2-trifluoromethylphenyl)-7-oxo-pyrazolo[1,5-a][1,3,5]triazine-2-sulphonamide | |
| 58 | N—(2-Difluoromethoxy-6-methylphenyl)-6,7-dihydro-5,6-dimethyl-3-methoxycarbonyl-7-oxopyrazolo[1,5-a][1,3,5]triazine-2-sulphonamide | |
| 59 | 6,7-Dihydro-5,6-dimethyl-N—(3,6-dimethyl-2-nitrophenyl)-3-methoxycarbonyl-7-oxo-pyrazolo[1,5-a][1,3,5]triazine-2-sulphonamide | |
| 60 | N—[2,6-Bis(difluoromethoxyphenyl)]6-Bis(difluoromethoxyphenyl)]-6,7-dihydro-5,6-dimethyl-3-methoxycarbonyl-7-oxo-pyrazolo[1,5-a][1,3,5]triazine-2-sulphonamide | |
| 61 | 6,7-Dihydro-5,6-dimethyl-N—(6-fluoro-2-methoxycarbonyl-3-methylphenyl)-3-methoxycarbonyl-7-oxo-pyrazolo[1,5-a][1,3,5]triazine-2-sulphonamide | |
| 62 | 6,7-Dihydro-5,6-dimethyl-3-methoxycarbonyl-N—(2-methoxy-6-trifluoromethylphenyl)-7-oxo-pyrazolo[1,5-a][1,3,5]triazine-2-sulphonamide | |

| Example No | Name of Compound | Physical Constant |
|---|---|---|
| 63 | 6,7-Dihydro-5,6-dimethyl-3-methoxycarbonyl-7-thioxo-N—(2-trifluoromethylphenyl)-pyrazolo[1,5-a][1,3,5]triazine-2-sulphonamide | |
| 64 | 6,7-Dihydro-5,6-dimethyl-N—(5,6-dimethyl-2-nitrophenyl)-3-methoxycarbonyl-7-thioxo-pyrazolo[1,5-a][1,3,5]triazine-2-sulphonamide | |
| 65 | N—(2-Bromo-6-chlorophenyl)-6,7-dihydro-5,6-dimethyl-3-methoxycarbonyl-7-thioxo-pyrazolo[1,5-a][1,3,5]triazine-2-sulphonamide | |
| 66 | N—(2-Bromo-6-chloro-3-methylphenyl)-6,7-dihydro-5,6-dimethyl-3-methoxycarbonyl-7-thioxopyrazolo[1,5-a][1,3,5]triazine-2-sulphonamide | |
| 67 | N—(2-Bromo-6-chloro-5-methylphenyl)-6,7-dihydro-5,6-dimethyl-3-methoxycarbonyl-7-thioxopyrazolo[1,5-a][1,3,5]triazine 2-sulphonamide | |
| 68 | N—(2-Dibromo-3-methylphenyl)-6,7-dihydro-5,6-dimethyl-3-methoxycarbonyl-7-thioxo-pyrazolo[1,5-a][1,3,5]triazine-2-sulphonamide | |
| 69 | 6,7-Dihydro-5,6-dimethyl-3-methoxycarbonyl-N—(6-methyl-2-trifluoromethylphenyl)-7-thioxo-pyrazolo[1,5-a][1,3,5]triazine-2-sulphonamide | |
| 70 | N—(2-Difluoromethoxy-6-methylphenyl)-6,7-dihydro-5,6-dimethyl-3-methoxycarbonyl-7-thioxopyrazolo[1,5-a][1,3,5]triazine-2-sulphonamide | |
| 71 | 6,7-Dihydro-5,6-dimethyl-N—(3,6-dimethyl-2-nitrophenyl)-3-methoxycarbonyl-7-thioxo-pyrazolo[1,5-a][1,3,5]triazine-2 sulphonamide | |
| 72 | N—[2,6-Bis(difluoromethoxyphenyl)]6-Bis(difluoromethoxyphenyl)]-6,7-dihydro-5,6-dimethyl-3-methoxycarbonyl-7-thioxo-pyrazolo[1,5-a][1,3,5]triazine-2-sulphonamide | |
| 73 | 6,7-Dihydro-5,6-dimethyl-N—(6-fluoro-2-methoxycarbonyl-3-methylphenyl)-3-methoxycarbonyl-7-thioxopyrazolo[1,5-a][1,3,5]triazine-2-sulphonamide | |
| 74 | 6,7-Dihydro-5,6-dimethyl-3-methoxycarbonyl-N—(2-methoxy-6-trifluoromethylphenyl))-7-thioxo-pyrazolo[1,5-a][1,3,5]triazine-2-sulphonamide | |
| 75 | N—(2-Bromo-6-methoxyphenyl)-6,7-dihydro-5,6-dimethyl-3-ethoxycarbonyl-7-thioxo-pyrazolo[1,5-a][1,3,5]triazine-2-sulphonamide | mp: 210° C. |
| 76 | 3-Carbamoyl-N—(2-carboxy-6-methylphenyl) 6,7-dihydro-5,6-dimethyl-7-oxopyrazolo-[1,5-a][1,3,5]triazine-2-sulphonamide | mp:257–258° C. |
| 77 | 3-Carbamoyl-N—(2-carboxy-6-methylphenyl)-6,7-dihydro-5,6-dimethyl-7-thioxopyrazolo-[1,5-a][1,3,5]triazine-2-sulphonamide | mp:267–268° C. |

The following examples illustrate the posibilties for areas of use of the compounds of the invention.

EXAMPLE A

Seeds of mono- and dicotyledenous plant species were sown in trays in humus-containing sandy soil and covered with earth. The compounds of the invention were applied as suspensions in 500 liters water/ha at a rate of 0.3 kg active ingredient/ha. to the soil surface before emergence of the plants.

After the treatment the test pots were put in a greenhouse and the test plants cultivated under good growing conditions. Three weeks after the treatment plant damage was assessed. Untreated controls were used for comparison.

As the table clearly shows numerous plant species weeds were destroyed or damaged. Wheat and barley were ressistant to the treatment.

In the following table:

| Compounds of invention | Tr | Ho | Br | He | St | Ab | Ma | Vi | Ch | So | Ec | Se | Ga |
|---|---|---|---|---|---|---|---|---|---|---|---|---|---|
| Example 1 | 0 | 0 | 3 | 3 | 2 | 3 | 4 | 4 | 4 | 3 | 3 | 3 | 3 |
| Example 2 | 2 | 2 | 3 | 3 | 2 | 2 | 4 | 3 | 3 | 4 | 4 | 3 | 3 |
| Example 3 | 0 | 0 | 3 | 3 | 1 | 2 | 4 | 3 | 3 | 3 | 3 | 4 | 2 |
| Example 4 | 1 | 0 | 3 | 3 | 3 | 3 | 4 | 3 | 3 | 3 | 3 | 4 | 4 |
| Example 5 | 0 | 0 | 3 | 3 | 3 | 3 | 4 | 3 | 4 | 2 | 2 | 2 | 3 |
| Example 6 | 0 | 1 | 2 | 3 | 3 | 2 | 4 | 4 | 4 | 3 | 3 | 2 | 4 |
| Example 7 | 0 | 1 | 2 | 3 | 2 | 2 | 4 | 3 | 3 | 2 | 2 | 2 | 2 |
| Example 8 | 1 | 2 | 3 | 3 | 2 | 2 | 4 | 3 | 4 | 4 | 3 | 4 | 3 |
| Example 9 | 0 | 1 | 2 | 3 | 2 | 2 | 4 | 3 | 3 | 3 | 2 | 3 | 3 |
| Example 10 | 1 | 1 | 3 | 3 | 3 | 2 | 4 | 3 | 3 | 3 | 3 | 2 | 3 |
| Example 15 | 0 | — | 1 | 1 | — | 0 | 4 | 0 | — | — | — | 0 | 0 |
| Example 16 | 1 | — | 1 | 2 | — | 0 | 4 | — | — | — | — | 1 | 2 |
| Example 17 | 0 | — | 3 | 3 | — | 3 | 4 | — | — | — | — | 3 | 3 |
| Example 18 | 0 | — | 3 | 3 | — | 3 | 3 | — | — | — | — | 2 | 2 |
| Example 19 | 0 | — | 3 | 3 | — | 3 | 4 | — | — | — | — | 2 | 2 |
| Example 20 | 0 | — | 3 | 2 | — | 1 | 4 | — | — | — | — | 0 | 2 |
| Example 21 | 1 | — | 3 | 2 | — | 1 | 4 | — | — | — | — | 3 | 3 |
| Example 22 | 0 | — | — | — | — | 3 | 4 | — | — | — | — | 4 | 4 |
| Example 23 | 0 | — | 3 | 3 | — | 3 | 4 | — | — | — | — | 3 | 3 |
| Example 24 | 0 | — | 0 | 0 | — | 0 | 3 | 1 | — | — | — | 0 | 0 |
| Example 25 | 0 | — | 3 | 3 | — | 2 | 4 | — | — | — | — | 2 | 4 |
| Example 26 | 0 | — | 3 | 2 | — | 2 | 4 | — | — | — | — | 0 | 2 |
| Example 27 | 1 | — | 2 | 2 | — | 1 | 4 | — | — | — | — | 0 | 2 |
| Example 28 | 0 | — | 2 | 1 | — | 0 | 3 | — | — | — | — | 0 | 3 |
| Example 29 | 1 | — | 3 | 2 | — | 0 | 4 | — | — | — | — | 0 | 3 |
| Example 30 | 0 | — | — | — | — | 3 | 4 | — | — | — | — | 4 | 4 |
| Example 39 | 0 | — | 3 | 3 | — | 0 | 4 | — | — | — | — | 3 | 3 |
| Example 42 | 1 | — | 3 | 3 | — | 0 | 4 | — | — | — | — | 3 | 3 |
| Example 45 | 0 | — | — | — | — | 0 | 2 | — | — | — | — | 1 | 2 |
| Example 46 | 0 | — | — | — | — | 2 | 4 | — | — | — | — | 2 | 3 |
| Example 47 | 0 | — | — | — | — | 0 | 3 | — | — | — | — | 0 | 2 |
| Example 48 | 0 | — | — | — | — | 1 | 4 | — | — | — | — | 2 | 4 |

-continued

| Compounds of invention | Tr | Ho | Br | He | St | Ab | Ma | Vi | Ch | So | Ec | Se | Ga |
|---|---|---|---|---|---|---|---|---|---|---|---|---|---|
| Control | 0 | 0 | 0 | 0 | 0 | 0 | 0 | 0 | 0 | 0 | 0 | 0 | 0 |

0 = no activity
4 - total destruction of the plant.
Tr = Triticum aestivum
Ho = Hordeum distichum
Br = Brassica napus napus
He = Helianthus annuus
St = Stellaria media.
Ab = Abutilon hybridum
Ma = Matricaria chamomilla
Vi = Viola tricolor
Ch = Chrysanthemum segetum
So = Sorghum sativum
Ec = Echinochloa crus-galli
Se = Setaria italica
Ga = Galium aparine
— = not tested

EXAMPLE B

Seeds of mono- and dicotyledenous plant species were sown in trays in humus-containing sandy soil and covered with earth. The compounds of the invention were applied as suspensions in 500 liters water/ha at a rate of 0.3 kg active ingredient/ha. to the soil surface after emergence of the plants.

After the treatment the test pots were put in a greenhouse and the test plants cultivated under good growing conditions. Two weeks after the treatment plant damage was assessed. Untreated contols were used for comparison.

As the table clearly shows numerous plant species weeds were destroyed or damaged. Wheat and barley were ressistant to the treatment.

In the following table:

| Compounds of invention | Tr | Ho | Br | Ly | Me | He | St | Ab | Ma | Vi | Ch | Ga |
|---|---|---|---|---|---|---|---|---|---|---|---|---|
| Example 1 | 0 | 0 | 3 | 4 | 3 | 3 | 4 | 2 | 3 | 2 | 3 | 4 |
| Example 2 | 1 | 0 | 3 | 3 | 3 | 4 | 2 | 3 | 3 | 3 | 3 | 3 |
| Example 3 | 0 | 0 | 3 | 3 | 4 | 3 | 3 | 2 | 2 | 3 | 2 | 3 |
| Example 4 | 1 | 2 | 4 | 4 | 3 | 4 | 4 | 2 | 3 | 1 | 4 | 4 |
| Example 5 | 0 | 0 | 2 | 3 | 3 | 3 | 2 | 2 | 3 | 3 | 4 | 3 |
| Example 6 | 0 | 0 | 3 | 4 | 3 | 4 | 3 | 2 | 4 | 2 | 4 | 4 |
| Example 7 | 0 | 0 | 3 | 3 | 3 | 3 | 2 | 3 | 2 | 2 | 2 | 3 |
| Example 8 | 0 | 2 | 3 | 3 | 3 | 3 | 4 | 3 | 3 | 2 | 4 | 4 |
| Example 9 | 0 | 0 | 2 | 2 | 2 | 2 | 3 | 1 | 2 | 1 | 2 | 3 |
| Example 10 | 0 | 0 | 2 | 3 | 2 | 3 | 3 | 2 | 2 | 2 | 3 | 3 |
| Control | 0 | 0 | 0 | 0 | 0 | 0 | 0 | 0 | 0 | 0 | 0 | 0 |

0 = no activity
4 - total destruction of the plant.
Tr = Triticum aestivum
Ho = Hordeum distichum
Br = Brassica napus napus
Ly = Lycopersicon esculentum
Me = Medicago sativa
He = Helianthus annuus
St = Stellaria media.
Ab = Abutilon hybridum
Ma = Matricaria chamomilla
Vi = Viola tricolor
Ch = Chrysanthemum segetum
Ga = Galium aparine

We claim:

1. 6,7-Dihydropyrazole[1,5-a][1,3,5]triazine-2-sulphonamides of formula I in which
Ar is phenyl, naphthyl, pyridyl or thienyl group of general formula $R_1$, $R_2$, $R_3$, $R_4$ and $R_5$ are the same or different and are hydrogen, a $C_1$-$C_6$-alkyl, $C_2$-$C_6$-alkenyl or $C_2$-$C_6$-alkynyl group, each of which is optionally substituted by one or more of the same or different halo, hydroxy, halo-$C_1$-$C_4$-alkyl, $C_1$-$C_4$-alkoxy, halo-$C_1$-$C_4$-alkoxy, $C_1$-$C_4$-alkylthio, $C_1$-$C_4$-alkylsulphinyl or $C_1$-$C_4$-alkylsulphonyl, halogen, $C_1$-$C_4$-alkoxy, a group $R_{10}$—O—CO, a carbamoyl group $R_{11}R_{12}N$—CO—, an amino group $R_{11}R_{12}N$—, cyano, nitro, a sulphur containing group $R_{10}$—S-

(O)$_n$—, an acyl group R$_{10}$—CO, a group R$_{10}$—O—CO—(CH$_2$)$_n$, or phenyl or phenoxy, both of which are optionally substituted by one of more of C$_1$-C$_4$-alkyl, halo or nitro, R$_6$ is hydrogen, an acyl group R$_{10}$—CO, a group R$_{10}$—O—CO—, C$_1$-C$_6$-alkyl, C$_2$-C$_6$-alkenyl, C$_2$-C$_6$-alkynyl, phenyl-C$_1$-C$_4$-alkyl, a carbamoyl group R$_{11}$R$_{12}$N—CO—, an alkali metal, an alkaline earth metal or ammonium group, optionally substituted by C$_1$-C$_6$-alkyl, R$_7$ and R$_8$ are the same or different and are hydrogen, a C$_1$-C$_6$-alkyl, C$_2$-C$_6$-alkenyl or C$_2$-C$_6$-alkynyl group, each of which is optionally substituted by halo or C$_1$-C$_4$-alkoxy, a phenyl-C$_1$-C$_6$-alkyl, phenyl-C$_2$-C$_6$-alkenyl or phenyl-C$_2$-C$_6$-alkynyl group, each of which is optionally substituted by halo, C$_1$-C$_4$-alkyl, C$_1$-C$_4$-alkoxy, C$_1$-C$_4$-alkoxy-C$_1$-C$_4$-alkyl or halo-C$_1$-C$_4$-alkyl, phenyl, substituted by R$_1$, R$_2$, R$_3$, R$_4$ and R$_5$, an acyl group R$_{10}$—CO, a group R$_{10}$—O—CO, a group R$_{10}$—O—CO—(CH$_2$)$_n$, a carbamoyl group R$_{11}$R$_{12}$N—CO—, or a sulphonyl group R$_{10}$—SO$_2$, R$_9$ is hydrogen, a C$_1$-C$_6$-alkyl, C$_2$-C$_6$-alkenyl or C$_2$-C$_6$-alkynyl group, each of which is optionally substituted by halo or C$_1$-C$_4$-alkoxy, a phenyl-C$_1$-C$_6$-alkyl, phenyl-C$_2$-C$_6$-alkenyl or phenyl-C$_2$-C$_6$-alkynyl group, each of which is optionally substituted by halo, C$_1$-C$_4$-alkyl, C$_1$-C$_4$-alkoxy, C$_1$-C$_4$-alkoxy-C$_1$-C$_4$-alkyl or halo-C$_1$-C$_4$-alkyl, phenyl, substituted by R$_1$, R$_2$, R$_3$, R$_4$ and R$_5$, an acyl group R$_{10}$—CO, a group R$_{10}$—O—CO, a group R$_{10}$—O—CO—(CH$_2$)$_n$, a carbamoyl group R$_{11}$R$_{12}$N—CO—, a sulphonyl group R$_{10}$—SO$_2$ or R$_{10}$—O—SO$_2$, cyano or nitro R$_{10}$ is hydrogen, a C$_1$-C$_6$-alkyl, C$_2$-C$_6$-alkenyl, C$_2$-C$_6$-alkynyl or phenyl-C$_1$-C$_4$-alkyl group, each of which is optionally substituted by one or more of the same or different halo, hydroxy or C$_1$-C$_4$-alkoxy, or phenyl, optionally substituted by halo, nitro or C$_1$-C$_4$-alkyl, R$_{11}$ and R$_{12}$ are the same or different and are hydrogen, a C$_1$-C$_6$-alkyl, C$_2$-C$_6$-alkenyl or C$_2$-C$_6$-alkynyl group, each of which is optionally substituted by one or more of the same or different halo, hydroxy or C$_1$-C$_4$-alkoxy, or R$_{11}$ and R$_{12}$ together with the adjacent nitrogen form a pyrrolidinyl, piperidino or morpholino ring, X is oxygen or sulphur, and n is 0, 1 or 2.

2. 6,7-Dihydropyrazole[1,5-a][1,3,5]triazine-2-sulphonamides according to claim 1, in which Ar is a phenyl group of general formula

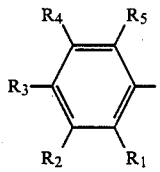

R$_1$ and R$_5$ are the same or different and are halogen, methyl, trifluoromethyl, nitro, methoxy or methoxycarbonyl, R$_2$, R$_3$ and R$_4$ are the same or different and are hydrogen, halogen, trifluoromethyl or a C$_1$-C$_4$-alkyl group, R$_6$ is hydrogen, said metal or a C$_1$-C$_4$-acyl group, R$_7$ and R$_8$ are the same or different and are hydrogen, C$_1$-C$_4$-acyl, C$_1$-C$_6$-alkyl, C$_2$-C$_4$-alkenyl or phenyl, and R$_9$ is hydrogen, a C$_1$-C$_4$-acyl group, a group R$_{10}$—O—CO, a carbamoyl group R$_{11}$R$_{12}$N—CO—, a sulphonyl group R$_{10}$—SO$_2$, cyano or nitro.

3. A herbicidal and plant-growth regulant composition with comprises an effective herbicidal and plant growth regulant amount of a compound according to claim 1, in admixture with carriers and diluents.

4. A method of combating weeds which comprises applying to the weeds or their locus an effective herbicidal amount of a compound according to claim 1.

5. A method of regulating the growth of plants which comprises applying to the plants or their locus a plant growth regulant amount of a compound according to claim 1.

6. A herbicidal and plant-growth regulant composition which comprises a compound according to claim 2, in admixture with carriers and diluents.

7. A method of combating weeds which comprises applying to the weeds or their locus a compound according to claim 2.

8. A method of regulating the growth of plants which comprises applying to the plants or their locus a plant growth regulant amount of a compound according to claim 2.

9. N-(2,6-disubstituted phenyl)-6,7-dihydro-5,6-dimethyl-3-methoxycarbonyl-pyrazolo[1,5-a][1,3,5]triazine-2-sulfonamide according to claim 2, in which the substituents are individually selected from the group consisting of halogen, methyl, nitro and methoxy.

10. N-(2,6-disubstituted phenyl)-6,7-dihydro-5,6-dimethyl-3-methoxycarbonyl-pyrazolo[1,5-a][1,3,5]triazine-2-sulfonamide according to claim 9 in which said substituents are individually selected from the group consisting of chloro, fluoro and methyl and X is S.

11. A method of regulating the growth of plants which comprises applying to the plants or their locus a plant growth regulant amount of a compound according to claim 9.

12. A method of regulating the growth of plants which comprises applying to the plants or their locus a plant growth regulant amount of a compound according to claim 10.

13. A method of combatting weeds which comprises applying to the weeds or their locus an effective herbicidal amount of a compound according to claim 9.

14. A method of combatting weeds which comprises applying to the weeds or their locus an effective herbicidal amount of a compound according to claim 10.

15. A herbicidal and plant-growth regulant composition which comprises an effective herbicidal and plant growth regulant amount of a compound according to claim 9, in admixture with carriers and diluents.

16. A herbicidal and plant-growth regulant composition which comprises a compound according to claim 10 in admixture with carriers and diluents.

* * * * *